United States Patent
Bush

(10) Patent No.: US 7,932,249 B2
(45) Date of Patent: Apr. 26, 2011

(54) OLANZAPINE PAMOATE DIHYDRATE

(75) Inventor: Julie Kay Bush, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 882 days.

(21) Appl. No.: 11/722,228

(22) PCT Filed: Dec. 22, 2005

(86) PCT No.: PCT/US2005/046752
§ 371 (c)(1),
(2), (4) Date: Jun. 20, 2007

(87) PCT Pub. No.: WO2006/073886
PCT Pub. Date: Jul. 13, 2006

(65) Prior Publication Data
US 2008/0096871 A1    Apr. 24, 2008

Related U.S. Application Data

(60) Provisional application No. 60/641,693, filed on Jan. 5, 2005.

(51) Int. Cl.
*A61P 25/18* (2006.01)
*A61K 31/5513* (2006.01)
*C07D 495/04* (2006.01)

(52) U.S. Cl. .................. 514/220; 540/557
(58) Field of Classification Search ............ 514/220; 540/557
See application file for complete search history.

(56) References Cited

U.S. PATENT DOCUMENTS

| | | |
|---|---|---|
| 3,354,036 A | 11/1967 | Jelinek |
| 3,676,557 A | 7/1972 | Lachman et al. |
| 3,904,670 A | 9/1975 | Ricard et al. |
| 3,956,330 A | 5/1976 | Corey, Jr. et al. |
| 4,016,273 A | 4/1977 | Sieger et al. |
| 4,076,942 A | 2/1978 | Smith et al. |
| 4,320,124 A | 3/1982 | Koe |
| 4,594,357 A | 6/1986 | Dell et al. |
| 4,675,189 A | 6/1987 | Kent et al. |
| 4,906,474 A | 3/1990 | Langer et al. |
| 4,977,150 A | 12/1990 | Chakrabarti |
| 5,229,382 A | 7/1993 | Chakrabarti et al. |
| 5,292,760 A | 3/1994 | Martin et al. |
| 5,439,688 A | 8/1995 | Orsolini et al. |
| 5,605,897 A | 2/1997 | Beasley, Jr. et al. |
| 5,612,346 A | 3/1997 | Mesens et al. |
| 5,639,480 A | 6/1997 | Bodmer et al. |
| 5,643,604 A | 7/1997 | Uribe et al. |
| 5,693,336 A | 12/1997 | Moynihan |
| 5,723,467 A | 3/1998 | Mesens et al. |
| 5,736,152 A | 4/1998 | Dunn |
| 5,736,541 A | 4/1998 | Bunnell et al. |
| 5,773,032 A | 6/1998 | Engel et al. |
| 5,776,885 A | 7/1998 | Orsolini et al. |
| 5,776,928 A | 7/1998 | Beasley, Jr. |
| 6,169,084 B1 | 1/2001 | Bunnell et al. |
| 6,617,321 B2 | 9/2003 | Allen et al. |
| 7,303,764 B2 | 12/2007 | Allen et al. |

FOREIGN PATENT DOCUMENTS

| | | |
|---|---|---|
| EP | 0214501 | 3/1987 |
| EP | 0487674 B1 | 6/1992 |
| EP | 0215313 | 7/1992 |
| EP | 0569096 | 11/1993 |
| EP | 0454436 | 9/1995 |
| GB | 1343936 | 1/1974 |
| GB | 1539277 | 1/1979 |
| JP | 1284333 A | 5/1988 |
| JP | 7196510 A | 12/1993 |
| JP | 9157159 A | 12/1995 |
| WO | 94/10982 A1 | 5/1994 |
| WO | 96/15815 A1 | 5/1996 |
| WO | 96/29995 A1 | 10/1996 |
| WO | 96/30374 A1 | 10/1996 |
| WO | 96/30375 A1 | 10/1996 |
| WO | 96/32948 A1 | 10/1996 |
| WO | 96/38151 A1 | 12/1996 |
| WO | 96/38152 A1 | 12/1996 |
| WO | 97/09985 A1 | 3/1997 |
| WO | 98/11893 A1 | 3/1998 |
| WO | WO-03/037903 A1 | 5/2003 |
| WO | 2006/073886 A1 | 7/2006 |

OTHER PUBLICATIONS

Berge et al., "Pharmaceutical Salts", J. Pharm. Sci., vol. 66, No. 1, pp. 1-19 (Jan. 1977).
Van Der Sluis et al., "Solvents and X-Ray Crystallography", J. Of Crystal Growth 97, pp. 645-656 (1989).
Caldwell et al., "Latentiation of dihydrostreptomycin by pamoate dormation", J. Pharm. Sci., pp. 1689-1690 (Jun. 1970).
Citrome, "Olanzapine pamoate: a stick in time? A review of the efficacy and safety profile of new depot formulation of a second-generation antipsychotic", Int. Journal of Clinical Practice, vol. 63 (1), 140-150, (Jan. 2009).
Coatney et al., "Further observation on the antimalarial activity of CI-501 (Camoloar) against the chesson strain of vivax malaria", Laboratory of Parasite Chemotherapy, National Institute of Allergy and Infectious Diseases, National Institutes of Health, Bethesda, MD, pp. 383-385, 1964.
Coleman et al., Biopharmaceutics & Drug Disposition, vol. 7, pp. 173-182 (1986).
Coleman et al., Pharm. Pharmacolo. vol. 37, pp. 878-883 (1985).

(Continued)

*Primary Examiner* — Brenda L Coleman
(74) *Attorney, Agent, or Firm* — Ted Joseph Ebersole; Nelsen L. Lentz

(57) ABSTRACT

The present invention relates olanzapine pamoate dihydrate, pharmaceutical compositions thereof and use in treating certain mental disorders, such as schizophrenia.

3 Claims, No Drawings

OTHER PUBLICATIONS

Diamond et al., Current Therapeutic Research, vol. 7(3), pp. 170-175 (1965).
Elsager, Edward, Human Antiparasitic Agents, Chapter 14a, Ann. Rep. Med. Chem, pp. 136-149, (1965).
Florence et al., "Effect of formulation of intramuscular injections of phenothiazines on duration of activity", Journal of Pharmaceutical Sciences, vol. 65(11), pp. 1665-1668, (1976).
Goldberg et al., "A double-blind study of tofrani pamoate vs. tofrani hydrochloride", Psychosomatics, vol. XIII, pp. 131-134 (Mar.-Apr. 1972).
Gould, "Salt Selection for basic drugs", Int. Journal of Pharmceuticals, vol. 33, pp. 201-217 (1986).
Injectable Product-Fundamentals, Preparation of Drug and Application, 1st edition, pp. 20-21 (1995).
Khorana, Indian Journal of Physiology and Pharmacology, vol. 25(4), pp. 331-338 (1989).
Miller et al., "A controlled study of single-dose administration of imipramine pamoate in endogenous depression", Current Therapeutic Research, vol. 15, No. 9. 10, (Oct. 1973).
Saias et al., English translation, "A class of oral retard and sustained effort drugs: the pamoates", Annales Pharmaceutiques francaises, vol. 27 (9-10), pp. 557-570 (1969).
Saias et al., French version, "A class of oral retard and sustained effort drugs: the pamoates", Annales Pharmaceutiques francaises, vol. 27 (9-10), pp. 557-570 (1969).
Sustained and Controlled Release Drug Delivery Systems, edited by Robinson, passim (pp. 4, 5, 47, 48, 136, 137, 175, 358-360, 412-415, 462) (1978).
Thompson et al., "Laboratory studies on 4,6,-diamino-1-(p-chlorophenyl)-1,2-dihydro-2,2-dimethyl-s-triazine pamoate (CI-501) as a repository antimalarial drug", Research Div., Parke, Davis & Company, Ann Arbor, MI, pp. 481-493, 1965.
Affidavit of Expert Dr. Arvind Kumar Bansal filed in Indian Opposition relating to Indian Patent No. 220287 (Eli Lilly), Nov. 26, 2009.
PCT/US98/20426 International Search Report Jan. 12, 1999.
PCT/US99/06417International Search Report Jul. 27, 1999.
Felberbaum, "Treatment of uterine fibroids with a slow release formulation of the gonadotrophin releasing hormone antagonist Cetrorelix", Hum Reprod vol. 13(6), pp. 1660-1668, (1998).
Randell et al., "Prolonged Analgesia after Epidural Injection of a Poorly Soluble Salt of Fentanyl", Anesth Analg. vol. 79, pp. 905-910 (1994).
Silverman et al., "A case of Accidental Parenteral Injection of Povan", Toxicology and Applied Pharmacology vol. 16 (3), pp. 740-742 (May 1970).
Wells, Pharmaceutical Preformulation: The Physiochemical Properties of Drug Substances, ISBN 0-7458-0276-1, Section 2.3, pp. 28-40 (1998).
Chile search results from Application No. 585-99, Mar. 29, 1999.
Chile written answering opposition and English translation, Application No. 585-99, Sep. 2000.
Colombia Opposition filed against application No. 99-018,903 (Spanish with English translation), Aug. 2001.
Colombia Response to Opposition 99-018,903 (Spanish with English translation).pdf, Aug. 2002.
Ecuador Oppostion SP 94-1212 (Spanish with English translation), Jan. 2000.
Ecuador Response to Opposition SP 99-2901 (Spanish with English translation).pdf, Dec. 1999.
Ecuador Search Report SP 99-2901 2004.
European Search Report EP99915009.pdf, Oct. 26, 2001.
European Supplemental Partial European Search Report from EP 98949632 Apr. 19, 2006.
Hungarian Search Report for HU P0004534 Oct. 29, 2002.
Hungarian Search Report for HU P0103636 Apr. 17, 2003.
Indian Notice of Opposition re Patent 220287, May 2009.
Indian Notice of Opposition re Patent 220287, Johnson Affidavit, Aug. 2009.
Indian Notice of Opposition re Patent 220287, Mitchell Affidavit, Aug. 2009.
Opposition re IN Patent No. 220287, Reply Evidence by Opponent and index, Sep. 2009.
Japanese official action in JP 2000-513467 Jun. 2, 2009 with associate letter.
Exhibit 11, book entitled "Novel Drug Delivery Systems", Chapter 8, 1992.
Exhibit 14, "Salt Forms of Drugs and Adsorption", Encyclopedia of Pharmaceutical Technology vol. 13, Marcel Dekker, Inc. (1995).
Exhibit 15, Psychopharmacologic drugs Advisory Committee Briefing document for Zyprexa Olanzapine Pamoate (OP) report that was submitted to the US FDA by Lilly, Feb. 2008.
Exhibit 16, summary product characteristics of ZypAdhera (Olanzapine Pamoate long action injection) available at EMEA website, Feb. 2008.
Exhibit 17, article entitled "Upcoming agents for the treatment of schizophrenia, mechansim of action, efficacy and tolerability" published in Drugs vol. 68 (16): pp. 2269-2292 (2008).
Notice of Intent to Issue Ex Parte Reexamination Certificate, May 24, 2010, U.S. Appl. No. 90/010,584.

OLANZAPINE PAMOATE DIHYDRATE

This application is a national stage entry under 35 U.S.C. §371 of PCT/US05/46752, filed Dec. 22, 2005 which claims benefit of Provisional Application No. 60/641,693, filed Jan. 5, 2005.

BACKGROUND OF THE INVENTION

Olanzapine has shown great promise in the treatment of patients suffering from schizophrenia and is currently being marketed for that purpose. However, such patients are often non-compliant, making it difficult to assess whether or not a patient has received the proper dosage of medication. It is therefore desirable to formulate olanzapine in a sustained release or depot formulation to assure consistent and proper dosage of the drug substance and to assume compliance. U.S. Pat. No. 6,169,084 B1 discloses certain olanzapine pamoate salts and solvates thereof, such as the olanzapine pamoate monohydrate, which are useful in preparing such sustained release or depot formulations.

In order to achieve a sustained release formulation of 2 to 4 weeks, for example, an injectable, slow to dissolve form of the active compound is needed. Surprisingly, olanzapine pamoate can be prepared in the dihydrate form. In addition, olanzapine pamoate dihydrate is substantially less soluble in aqueous solution than olanzapine pamoate monohydrate. Thus, the olanzapine pamoate dihydrate has excellent properties for use as a depot preparation.

SUMMARY OF THE INVENTION

The present invention provides a compound which is olanzapine pamoate dihydrate.

The present invention further provides a pharmaceutical composition comprising olanzapine pamoate dihydrate and a pharmaceutically acceptable carrier, diluent, or excipient.

In addition, the present invention provides olanzapine pamoate dihydrate which is substantially pure.

The present invention also provides a method of treating schizophrenia, acute mixed or manic episodes associated with bipolar I disorder, agitation associated with schizophrenia, agitation associated with bipolar I disorder, agitation associated with dementia, or borderline personality disorder, comprising administering to a patient an effective amount of olanzapine pamoate dihydrate.

DETAILED DESCRIPTION OF THE INVENTION

XRPD Analysis

The X-ray powder diffraction (XRPD) pattern is obtained on a Siemens D5000 X-ray powder diffractometer, equipped with a CuKα source (λ=1.54056 Å) and a Kevex solid state Si(Li) detector, operating at 50 kV and 40 mA. Each sample is scanned between 4° and 40° in 2θ, with a step size of 0.02° in 2θ and a scan rate of 3.0 seconds/step, and with 1 mm divergence and receiving slits and a 0.1 mm detector slit.

The dry powder is packed into recessed top-loading sample holders and a smooth surface is obtained using a glass slide.

The dihydrate may be identified by the presence of peaks at 8.1±0.1, 9.8±0.1, 13.6±0.1, 16.3±0.1, 21.6±0.1, and 22.1±0.1° in 2θ; when the pattern is obtained from a copper radiation source (λ=1.54056) at ambient temperature and 20-25% relative humidity. Peaks at 9.5±0.1, 16.0±0.1 and 20.2±0.1° in 2θ are also highly indicative of the presence of the dihydrate. It is understood by one of ordinary skill in the art that while relative peak intensities may vary due to changes in crystal habit, the characteristic peak positions of the polymorph remain unchanged.

The angular peak positions in 2θ and corresponding $I/I_O$ data for all dihydrate peaks with intensities equal to or greater than 10% of the largest peak are tabulated in Table 2. All data in Table 2 is expressed with an accuracy of ±0.1° in 2θ.

TABLE 2

Angular Peak Positions in 2θ for Olanzapine Pamoate Dihydrate.

| Angle (° 2θ) | $I/I_o$ (%) |
|---|---|
| 6.4 | 14.0 |
| 8.1 | 90.6 |
| 9.5 | 33.5 |
| 9.8 | 64.8 |
| 10.8 | 18.2 |
| 11.6 | 10.5 |
| 12.7 | 11.3 |
| 13.1 | 24.4 |
| 13.6 | 60.3 |
| 14.4 | 11.7 |
| 15.3 | 21.1 |
| 15.7 | 14.0 |
| 16.0 | 39.8 |
| 16.3 | 100.0 |
| 18.2 | 11.2 |
| 18.5 | 11.5 |
| 19.0 | 20.2 |
| 20.0 | 16.5 |
| 20.2 | 41.5 |
| 20.5 | 11.2 |
| 21.6 | 68.0 |
| 22.1 | 57.6 |
| 22.4 | 13.2 |
| 22.7 | 11.7 |
| 23.3 | 19.9 |
| 23.5 | 17.8 |
| 24.8 | 16.1 |
| 25.3 | 10.2 |

Solid State NMR $^{13}$C Cross polarization/magic angle spinning (CP/MAS) NMR (solid-state NMR or SSNMR) spectra is obtained using a Varian Unity Inova 400 MHz NMR spectrometer operating at a carbon frequency of 100.573 MHz and equipped with a complete solids accessory and a Chemagnetics 4.0 mm T3 probe. Ramped-amplitude cross polarization (RAMP-CP) at 62 kHz and TPPM decoupling at 62-70 kHz are used. Acquisition parameters are as follows: 90° proton r.f. pulse width 4.0 μs, contact time 1.0 ms, pulse repetition time 10 s, MAS frequency 10.0 kHz, spectral width 50 kHz, and acquisition time 50 ms. Chemical shifts are referenced to the methyl group of hexamethylbenzene (δ=17.3 ppm) by sample replacement.

The dihydrate is analyzed via solid-state $^{13}$C nuclear magnetic resonance (NMR) spectroscopy. Solid state $^{13}$C chemical shifts reflect the molecular structure and electronic environment of the molecule in the crystal. The spectrum for the dihydrate comprises isotropic peaks at the following chemical shifts: 15.5, 43.6, 121.5, 123.2, 124.6, 127.3, 128.3, 130.3, 136.6, 148.8, and 162.4 ppm.

More specifically, the olanzapine pamoate dihydrate can be characterized by at least one of the following:

a) an X-ray powder diffraction obtained from a copper radiation source at ambient temperature containing 2-theta values at 8.1±0.1, 9.8±0.1, 13.6±0.1, 16.3±0.1, 21.6±0.1, and 22.1±0.1°; and b) a solid-state $^{13}$C nuclear magnetic resonance spectrum with peaks at the following chemical shifts 15.5, 43.6, 121.5, 123.2, 124.6, 127.3, 128.3, 130.3, 136.6, 148.8, and 162.4 ppm.

The reagents and materials for the present invention can be purchased or prepared by a variety of procedures well known to those of ordinary skill in the art. Olanzapine can be prepared by one of ordinary skill in the art, for example as described in U.S. Pat. Nos. 5,229,382 and 5,736,541. In addition, olanzapine pamoate and olanzapine pamoate monohydrate can be prepared by one of ordinary skill in the art, for example as set forth in U.S. Pat. No. 6,169,084 B1.

As used herein the term "substantially pure" refers to pure crystalline form of the compound comprising greater than about 90% of the desired crystalline form, and preferably greater than about 95% of the desired crystallzine form.

It is understood by one of ordinary skill in the art that olanzapine has the following structure:

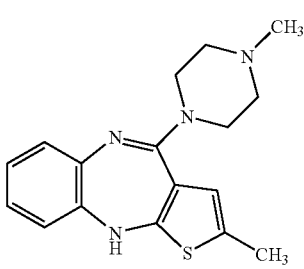

The examples set forth herein represent typical syntheses of the compounds of the present invention.

As used herein, the terms listed in the following table have the corresponding meanings as indicated:

| Term | Meaning |
|---|---|
| $^1$H NMR | Proton nuclear magnetic resonance spectroscopy |
| ss NMR | Solid state nuclear magnetic resonance spectroscopy |
| XRD | X-Ray Diffraction |
| XRPD | X-Ray Powder Diffraction |
| eq. | equivalents |
| g | grams |
| mg | milligrams |
| L | liters |
| mL | milliliters |
| μL | microliters |
| mol | moles |
| mmol | millimoles |
| m.p. | melting point |
| min | minutes |
| h or hr | hours |
| ° C. | degrees Celsius |
| aq. | aqueous |
| Celite ® | diatomaceous earth filtering agent |
| RT or rt | room temperature |
| DMF | N,N-dimethylformamide |
| DMSO | methyl sulfoxide |
| EtOAc | ethyl acetate |
| THF | tetrahydrofuran |
| DME | 1,2-dimethoxyethane |
| EtOH | ethanol |
| MeOH | methanol |

Preparation 1

Preparation of 2-methyl-4-(4-methyl-1-piperazinyl)-10H-thieno[2,3-b][1,5]benzodiazepine pamoate (olanzapine pamoate, See for Example Preparation 3 in U.S. Pat. No. 6,169,084 B1)

Olanzapine (3.12 g, 0.01 mole) is dissolved in tetrahydrofuran (50 mL) with heating. Pamoic acid (3.88 g, 0.01 mole) is dissolved in tetrahydrofuran (100 mL) with heating. The two solutions are mixed and filtered through a pad of Celite® while it is still warm. The yellow solution is transferred to a Buchi flask and evaporated under reduced pressure (bath temperature 50° C.). After about 50 mL of solvent are removed ethanol (50 mL) is introduced and evaporation continued. A further 50 mL of ethanol is introduced after a further 50 mL of solvent is collected. Evaporation is continued until crystallization commences. The crystals are collected by filtration and dried under high vacuum at 120° C. m.p. 203-205° C.

Preparation 2

Preparation of 2-methyl-4-(4-methyl-1-piperazinyl)-10H-thieno[2,3-b][1,5]benzodiazepine pamoate (olanzapine pamoate monohydrate, See for Example Preparation 6 in U.S. Pat. No. 6,169,084 B1)

Into a suitable beaker equipped with a magnetic stirrer is added methyl sulfoxide (22 ml), pamoic acid (2.49 g, 6.41 mmol), and olanzapine (2.0 g, 6.40 mmol). The slurry is stirred at 20-25° C. to dissolve (about 20 minutes). The solution is added over 20 minutes to a 250 mL three-necked flask equipped with a mechanical stirrer and containing water (96 ml) at 40° C. After the addition is complete, the slurry is stirred about 20 minutes at 40° C., cooled to 20-25° C. over about 30 minutes, filtered, and washed with water (25 ml). The product is dried in vacuo at 50° C. to provide the title compound (4.55 g).

EXAMPLE 1

Preparation of 2-methyl-4-(4-methyl-1-piperazinyl)-10H-thieno[2,3-b][1,5]benzodiazepine pamoate dihydrate (olanzapine pamoate dihydrate)

Olanzapine pamoate monohydrate (500 mg) is slurried in 1:1 v/v acetonitrile-$H_2O$ (10 mL) for 6 days. After one day the color changes from bright yellow to pale yellow. The solids are isolated by vacuum filtration and washed with 1:1 v/v acetonitrile-$H_2O$ to provide the title compound (465 mg).

EXAMPLE 2

Additional Preparation of 2-methyl-4-(4-methyl-1-piperazinyl)-10H-thieno[2,3-b][1,5]benzodiazepine pamoate dihydrate. (olanzapine pamoate dihydrate)

Olanzapine pamoate (10 g) is dissolved in 1:1 v/v methyl sulfoxide-acetonitrile (250 mL) and filtered. Water (300 mL) is then added dropwise, rapidly. The solid precipitate is allowed to resonate for about one hour, then isolated by vacuum filtration. The filter cake is washed with water (50 mL), followed by acetonitrile (50 mL), and is then air-dried for 30 minutes to provide the title compound (9.5 g).

EXAMPLE 3

Additional Preparation of 2-methyl-4-(4-methyl-1-piperazinyl)-10H-thieno[2,3-b][1,5]benzodiazepine pamoate dihydrate. (olanzapine pamoate dihydrate)

A wet ethyl acetate solution (400 mL) of olanzapine pamoate (20 g) is seeded with olanzapine dihydrate and slurried for 6 days. The solids are isolated by vacuum filtration, washed copiously with wet ethyl acetate and air dried to provide the title compound (20 g).

Comparative In Vitro Dissolution Test

In-vitro dissolution testing was performed to compare the olanzapine release rates for olanzapine pamoate monohydrate and the olanzapine pamoate dihydrate. The experimental conditions for the dissolution test are provided in Table 3.

TABLE 3

Summary of Experimental Conditions.

| Dissolution Parameter | Test Conditions |
| --- | --- |
| Apparatus | USP Apparatus 2 (Paddle Apparatus) |
| Paddle Speed | 50 RPM |
| Media | 0.05% CTAB, pH 6.8 USP Buffer |
| Media Temperature | 37° C. |
| Media Volume | 1000 mL |
| Sample Introduction | Weighed dry powder (approx. 172 mg partial dose) |
| Sampling Timepoints | 0.25, 0.5, 0.75, 1, 2, 4, 6, 24 hours |

A comparison of the data as provided in Table 4 demonstrates that, under the above aqueous conditions, olanzapine pamoate dihydrate has a substantially lower release rate of olanzapine than the olanzapine pamoate monohydrate.

TABLE 4

Olanzapine Release After 24 hrs. at 50 rpm Paddle Speed.

| | Average % Olanzapine Release (n = 3) | | | | | | | |
| --- | --- | --- | --- | --- | --- | --- | --- | --- |
| Compound | 0.25 hr. | 0.5 hr. | 0.75 hr. | 1 hr. | 2 hrs. | 4 hrs | 6 hrs. | 24 hrs. |
| Olanzapine Pamoate Monohydrate | 27 | 39 | 46 | 52 | 62 | 73 | 77 | 83 |
| Olanzapine Pamoate Dihydrate | 19 | 26 | 30 | 33 | 40 | 45 | 47 | 59 |

Another dissolution experiment was performed in order to ensure that the media conditions used to generate the profiles in Table 4 were not solubility limiting. This experiment was performed using the same samples and media conditions but at a higher paddle speed to provide the data listed in Table 5. These data show that the chosen media conditions provided sufficient solubility for both the olanzapine pamoate dihydrate and the olanzapine pamoate monohydrate.

TABLE 5

Olanzapine Release After 24 and 36 hrs. at 100 rpm Paddle Speed.

| | % Olanzapine Release (n = 1) | |
| --- | --- | --- |
| Compound | 24 hrs. | 36 hrs. |
| Olanzapine Pamoate Monohydrate | 99 | 99 |
| Olanzapine Pamoate Dihydrate | 95 | 97 |

Rabbit Assay

New Zealand White rabbits are selected for the evaluation of sustained release or depot formulations because the size of their leg muscles facilitates dose administration and evaluation of the injection site. Three rabbits of the same sex are used for each formulation with selection based on availability. The rabbits are at least 5 months old and weigh between 2.5 to 5 kg. Rabbits are given a single injection with a 20- or 21-gauge needle into the biceps femoris. The dose volume varies with the concentration of the formulation but does not exceed 2 mL per injection. The rabbits are given 10 mg of olanzapine/kg body weight.

A 2 mL blood sample is collected from the medial ear artery or jugular vein into heparinized collection tubes once prior to dose administration and at 4 hours after dose administration and again daily after 1, 2, 7, 10, and 14 days. Plasma is harvested and plasma concentration of olanzapine is determined by HPLC. Formulations of the instant invention can be tested in the rabbit assay.

Dog Assay

The beagle dog is selected because much is known about the pharmacokinetics of olanzapine in dogs. Since there is no difference in the pharmacokinetics of olanzapine between the sexes, dog selection is not based on sex. Three dogs (male or female) are used for each formulation. The dogs are adults (>6 months old) and weighed between 8 to 21 kg. The dogs are given a single injection with a 20 or 21 gauge needle into the gluteal or biceps femoris muscle. The dose volume vary with the concentration of the formulation but does not exceed 2 mL per injection. The dogs are given 10 mg of olanzapine/kg of body weight.

At each time point, a 2 mL blood sample is collected from the jugular vein into heparanized collection tubes. Blood samples are collected once prior to dose administration and at various time points after dose administration throughout the 28-day period. Typical time points are at 0.5, 1, 2, 4, 8, and 24 hours after dose administration and once daily after 2, 4, 7, 14, 21, and 28 days. Plasma is harvested and plasma concentration of olanzapine is determined by HPLC.

In addition, the present invention provides a pharmaceutical composition, which comprises olanzapine pamoate dihydrate, and a pharmaceutically acceptable carrier, diluent, or excipient.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide sustained release of olanzapine pamoate dihydrate after administration to the patient by employing procedures well known in the art.

Preferably, the formulation has a prolonged sustained release of an effective amount of olanzapine after injection, such as intramuscular injection, for a period of greater than 7 days, more preferably at least 14 days, most preferably up to 30 days with a burst release of less than 15% active ingredient. The term "burst" is understood by those skilled in the art to mean the immediate release of active ingredient. In addition, a preferred formulation is injectable through a 21 gauge needle or smaller with an injection volume of 2 ml or less. Other desirable characteristics include the use of carriers or excipients that are toxicologically and pharmaceutically acceptable. For example, a certain amount of the olanzapine pamoate dihydrate is placed in a vial, which is then sterilized together with any additional contents and then sealed. Mixing with a suitable carrier just before use, may be provided with a complementary vial or other container containing the desired carrier. Water is an example of such a carrier. Formulations, including sustained release or depot formulations are desirable in unit dosage form suitable, preferably, for subcutaneous or intramuscular administration.

As used herein the term "patient" refers to a mammal, such as a mouse, guinea pig, rat, dog or human. It is understood that the preferred patient is a human.

As used herein, the terms "treating" or "to treat" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances. The compounds can be administered by a variety of routes including oral, rectal, transdermal, subcutaneous, intravenous, intramuscular, bucal or intranasal routes. Alternatively, the compound may be administered by continuous infusion.

Olanzapine is effective over a wide dosage range, the actual dose administered being dependent on the condition being treated. For example, in the treatment of adult humans, dosages of from about 0.25 to 200 mg, preferably from 1 to 30 mg, and most preferably 1 to 20 mg per day may be used. In addition, a sustained release or depot formulation can be adjusted to provide the desired dosage per day over a period of from several days to up to about one month.

I claim:

1. A compound which is olanzapine pamoate dihydrate.
2. A compound which is olanzapine pamoate dihydrate which is substantially pure.
3. A method of treating schizophrenia, acute mixed or manic episodes associated with bipolar I disorder, agitation associated with schizophrenia, agitation associated with bipolar I disorder, agitation associated with dementia, or borderline personality disorder, comprising administering to a patient an effective amount of olanzapine pamoate dihydrate.

* * * * *